(12) United States Patent
Zhai et al.

(10) Patent No.: US 8,754,272 B2
(45) Date of Patent: Jun. 17, 2014

(54) PROCESS FOR CIS-1-CHLORO-3,3,3-TRIFLUOROPROPENE

(71) Applicant: Honeywell International Inc., Morristown, NJ (US)

(72) Inventors: Yian Zhai, Amherst, NY (US); Andrew Joseph Poss, Kenmore, NY (US); Michael Van Der Puy, Amherst, NY (US); Rajiv Ratna Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/674,145

(22) Filed: Nov. 12, 2012

(65) Prior Publication Data

US 2013/0150632 A1   Jun. 13, 2013

Related U.S. Application Data

(60) Provisional application No. 61/567,669, filed on Dec. 7, 2011.

(51) Int. Cl.
*C07C 17/23* (2006.01)

(52) U.S. Cl.
USPC .......................... 570/156; 570/230

(58) Field of Classification Search
USPC ......................... 570/230, 155, 156
See application file for complete search history.

(56) References Cited

U.S. PATENT DOCUMENTS

| | | | |
|---|---|---|---|
| 2,590,433 A * | 3/1952 | Blum | 570/158 |
| 2,774,798 A * | 12/1956 | Chiang et al. | 570/158 |
| 5,616,819 A | 4/1997 | Boyce et al. | |
| 5,710,352 A | 1/1998 | Tung | |
| 5,714,655 A | 2/1998 | Yamamoto et al. | |
| 6,111,150 A | 8/2000 | Sakyu et al. | |
| 6,362,383 B1 | 3/2002 | Wilmet et al. | |
| 6,844,475 B1 | 1/2005 | Tung et al. | |
| 6,958,424 B1 | 10/2005 | Nair et al. | |
| 7,829,747 B2 | 11/2010 | Wang et al. | |
| 2007/0203368 A1 * | 8/2007 | Tortelli et al. | 568/685 |
| 2008/0103342 A1 | 5/2008 | Wang et al. | |
| 2011/0201853 A1 | 8/2011 | Tung et al. | |
| 2011/0218256 A1 * | 9/2011 | Yang et al. | 521/27 |
| 2012/0215041 A1 | 8/2012 | Nair et al. | |

FOREIGN PATENT DOCUMENTS

| | | | |
|---|---|---|---|
| WO | 2010059496 A1 | 5/2010 | |
| WO | 2010068715 A2 | 6/2010 | |

OTHER PUBLICATIONS

Paleta, O. et al. Bull. de la Societe Chimique de France 1986, 6, 920-924.*

PCT ISR & Written Opinion issued in PCT/US2012/066994 dated Mar. 18, 2013.

Henne, A. L. et al., J. Am. Chem. Soc., 64 (1942) 1157-9.

* cited by examiner

*Primary Examiner* — Jafar Parsa
*Assistant Examiner* — Medhanit Bahta
(74) *Attorney, Agent, or Firm* — Erika S. Wilson

(57) ABSTRACT

Disclosed is a process for the preparation of cis-1-chloro-3,3,3-trifluoropropene (cis-1233zd) comprising the steps of (a) providing $CF_3CHClCHCl_2$ (233da), and (b) treating the 233da with a dechlorinating agent to produce a mixture of compounds including cis-1-chloro-3,3,3-trifluoropropene, preferably wherein the amount of the cis-isomer generated in the reaction is not less than 30%.

22 Claims, No Drawings

PROCESS FOR CIS-1-CHLORO-3,3,3-TRIFLUOROPROPENE

CROSS-REFERENCE TO RELATED APPLICATION

This application claims domestic priority to commonly owned, U.S. Provisional Patent Application Ser. No. 61/567,669, filed Dec. 7, 2011, the disclosure of which is hereby incorporated herein by reference.

FIELD OF THE INVENTION

This invention relates to the preparation of hydrochlorofluoroolefins (HCFOs) which have negligible ozone depletion potential (ODP) and low global warming potential (GWP) and are suitable for use in applications such as blowing agents and solvents. More particularly, this invention relates to a processes for converting trans 1-chloro-3,3,3-trifluoropropene (trans-1233zd) which has a boiling point of 18.7° C., to the cis-isomer (cis-1233zd), which has a boiling point of 39.5° C.

BACKGROUND OF THE INVENTION

As described above, this invention related to the production of cis-1-chloro-3,3,3-trifluoropropene, which may be designated as HCFO-1233zd (Z), 1233zd(Z), or cis-1233zd. The preferred designation used herein is 1233zd(Z). 1233zd (Z) is a low global warming compound that has applications as a replacement for high global warming materials, for example in foam blowing and aerosol propellant applications.

The isomeric compounds 1233zd may be produced by a number of different methods. Examples include the dehydrochlorination of $CF_3CH_2CHCl_2$ (J. Am. Chem. Soc., 64 (1942) 1157-9); the dehydrofluorination of 3-chloro-1,1,1,3-tetrafluoropropane (U.S. Pat. No. 7,829,747), and the fluorination of halogenated propanes (U.S. Pat. Nos. 5,710,352, 6,111,150, and 6,844,475). Other methods are shown in U.S. Pat. Nos. 6,958,424 and 5,616,819. See also U.S. Patent Pub. No. 2008/0103342 and PCT Pub. No. WO 2010/059496). In most reactions the trans-isomer of 1233zd is the thermal dynamically favored product, with only about 3% to 5% of cis-isomer obtained in most manufacturing processes.

PCT Pub. No. WO 2010/068715 provides a process in which the trans-isomer of 1233zd can be isomerized over a fluorinated $Cr_2O_3$ catalyst in the vapor phase at a temperature of about 300° C. The resulting amount of the cis-isomer is only about 10%, combined with from about 2% to 3% of other materials. This process thus requires multiple repeated cycles in order to generate large quantities of the desired cis-isomer of 1233zd.

U.S. Patent Pub. No. 2012-0215041 A1 (Ser. No. 13/030,789) describes a process for the reduction of 1-chloro-3,3,3-trifluoropropyne with palladium under hydrogen atmosphere to stereospecifically generate cis-1233zd in 53% yield. However, unless the reduction process is carefully controlled, over reduction can occur, which leads to the compounds $CF_3CH=CH_2$ and $CF_3CH_2CH_3$.

Both the cis (or Z) isomer and the trans (or E) isomer of 1233zd have practical applications. The cis-isomer of HCFO-1233zd is more suitable for solvent applications than the trans isomer because of a higher boiling point.

U.S. Pat. No. 6,362,383 teaches a process for preparing 1,1,1,3,3-penta-fluoropropane (HFC-245fa) by (1) a first reaction step in which 1,1,1,3,3-pentachloro-propane (HCC-240fa) is reacted with hydrogen fluoride in the liquid phase in the presence of a first hydrofluorination catalyst under conditions that are suitable for obtaining a mixture of reaction products comprising 1-chloro-3,3,3-trifluoropropene (HCFO-1233zd) in substantial amount, and (2) a second reaction step in which the 1-chloro-3,3,3-trifluoropropene (HCFO-1233zd) obtained from the first step is reacted with hydrogen fluoride in the liquid phase in the presence of a second hydrofluorination catalyst, and preferably while hydrogen chloride is continuously fed in, in order to obtain 1,1,1,3,3-pentafluoropropane (HFC-245fa).

The disclosures of the foregoing references are hereby incorporated herein by reference.

Thus there remains a need for a process which makes 1233zd wherein a substantial portion of cis isomer is present or even more preferably, the process stereospecifically produces the cis-isomer of 1233zd.

SUMMARY OF THE INVENTION

The present invention provides processes for the manufacture of cis-1-chloro-3,3,3-trifluoropropene (1233zd (Z)) wherein the amount of the cis isomer is preferably not less than about 30%. More preferably the amount of the cis isomer is not less than about 35%. Most preferably, the amount of the cis isomer is not less than about 45%.

In one embodiment, the process comprises the steps of (a) providing 233da, namely $CF_3CHClCHCl_2$ and (b) treating 233da with a dechlorinating agent such as zinc or zinc complex, to generate the desired compound, cis-1-chloro-3,3,3-trifluoropropene.

In another embodiment, the process comprises the steps of (a) providing 233da, and (b) treating 233da with a dechlorinating agent such as copper, magnesium, or a zinc/copper mixture, to generate the desired compound, cis-1-chloro-3,3,3-trifluoro-propene.

The 233da can be provided in a number of ways such as the fluorination of chlorinated propanes and by the chlorination of trans-1233zd. The latter process thus essentially provides a means of isomerizing trans-1233zd to cis-1233zd.

Thus, another embodiment of the present invention comprises the steps of (a) the chlorination of trans-1233zd to produce 233da, and (b) treating 233da with a dechlorinating agent to generate the desired compound, cis-1233zd.

In certain embodiments, the 233da is provided by the fluorination of a chlorinated propane compound.

In certain embodiments a solvent is be used in the reaction. In certain embodiments the solvent is selected from the group consisting of alcohols, ethers, amides, carboxylic acids, and water. Preferably the solvent is selected from water, alcohol, mixtures thereof. More preferably, the solvent is water.

In certain embodiments, the process includes the use of a catalyst. Preferably the catalyst is selected from the group comprising a mineral acid or mixtures thereof. In certain embodiments the mineral acid catalyst comprises HCl. In certain embodiments the catalyst comprises a Lewis acid catalyst or mixtures thereof. Preferably, the Lewis acid catalyst comprises a metal salt or mixture of metal halide salts. More preferably, the metal salt comprises a zinc halide salt. Most preferably, the zinc halide salt comprises zinc chloride. In certain embodiments, the metal salt comprises a tin halide salt. Preferably, the tin halide salt comprises tin chloride.

In certain embodiments the reaction temperature range is less than the boiling point of the solvent. Thus, reaction temperatures employed herein can range from about 35° C. to about 100° C., preferably from about 55° C. to 90° C., more preferably from about 70° C. to 85° C., and most preferably from about 75° C. to about 82° C. Other temperatures can be used based on the reaction conditions.

In certain embodiments, the molar ratio of the dechlorinating agent to 233da is at least 1:1. Preferably, the molar ratio of the dechlorinating agent to 233da is from 1.1 to 2.5.

In yet another embodiment, the invention provides process for the preparation of cis-1-chloro-3,3,3-trifluoropropene comprising the steps of:
  (a) mixing a combination comprising zinc, solvent, and catalyst;
  (b) heating the mixture to within a few degrees of the selected reaction temperature;
  (c) adding HCFC-233da in a manner that controls the reaction temperature, as the production of 1233zd is exothermic;
  (d) running the reaction and adding 233da as need; and
  (e) collecting the 1233zd(Z) as it is produced.

In certain embodiments of this process, the 233da is added mechanically at a set rate that is slow enough to maintain the reaction temperature.

In certain embodiments of this process, the reaction heating is continued for a time to ensure that all the 233da has reacted.

Preferably, the 1233zd(Z) is removed from the processes as it is produced.

Yet another embodiment of this invention is directed to a process that generates 233da directly from a halogenated propane by fluorination, such as the fluorination of 1,1,1,2,3,3-hexachloropropane. Halogenated propane compounds can be fluorinated with HF using metal catalysts such as $SbCl_5$, $TiCl_4$, $SnCl_4$, $TaCl_5$, and $NbCl_5$ under variable temperatures.

In a typical reaction, metal catalyst is treated with anhydrous HF first in Monel autoclave at 70° C. to 90° C. until no further pressure increase is detected. Then, additional HF is charged into the autoclave followed by 1,1,1,2,3,3-hexachloropropane. The autoclave is sealed and heated to the desired reaction temperature, and held at that temperature for a certain amount of time. After work-up, the crude material is checked by GC and NMR and the desired compound 233da is isolated from the resulting mixture of products.

DETAILED DESCRIPTION OF THE INVENTION

As described above, the present invention provides a process for the manufacture of cis-1-chloro-3,3,3-trifluoropropene (1233zd (Z)) wherein the amount of the cis-isomer is not less than 30%. The process comprises the steps of (a) providing $CF_3CHClCHCl_2$ (233da), and (b) treating 233da with a dechlorinating agent to generate the desired compound, cis-1-chloro-3,3,3-trifluoropropene.

As described above, the 233da can be provided in a number of ways such as the fluorination of chlorinated propanes and by the chlorination of trans-1233zd. The latter process thus essentially provides a means of isomerizing trans-1233zd to cis-1233zd.

A variety of solvents can be used for the dechlorination of 233da. Suitable solvents include alcohols, ethers, amides, carboxylic acids, water. Water and alcohols are preferred with water being most preferred. If desired, no solvent need be employed.

Catalysts can also be used. These include mineral acids such as HCl or Lewis acids such as metal salts, especially those of zinc and tin (e.g., $ZnCl_2$, $SnCl_2$, and the like). Depending on the activity of the zinc used, the catalyst may not be necessary.

Reaction temperatures, for reactions at atmospheric pressure, are limited to the boiling point of the solvent, but the reaction may proceed at temperatures well below the boiling point of the solvent. To find the appropriate reaction temperature, a portion of 233da is added to the Zn/catalyst/solvent mixture and heating is continued until evidence of reaction is observed (heat release or generation of volatile 1233zd).

Thus, typical reaction temperatures employed herein can range from about 35° C. to about 100° C., preferably from about 55° C. to 90° C., more preferably from about 70° C. to 85° C., and most preferably from about 75° C. to about 82° C. Other temperatures can be used based on the reaction conditions.

The molar ratio of zinc to 233da should be at least one, and can be higher, but ratios in excess of 3 are not particularly advantageous, and may make stirring more difficult. Molar ratios of zinc to 233da are typically in the range of 1.1 to 2.5.

In a typical reaction, zinc, solvent, and catalyst are mixed and heated to within a few degrees of the selected reaction temperature. 233da is then added over time to control the reaction, as the production of 1233zd is exothermic. The temperature of the reaction mixture may increase 5 to 10 degrees initially and is then allowed to return to the original reaction temperature before another portion of 233da is added.

Alternatively, 233da may be added mechanically at a set rate that is slow enough to maintain the desired reaction temperature. After the addition is heating is continued fat the reaction temperature for a sufficient time to ensure that all the 233da has been reacted. Generally, it is advantageous to remove 1233zd as it is formed, but this is not required.

EXAMPLE 1

Preparation of 233da

Chlorine gas (625 g, 8.80mol) was bubbled into the trans-1233zd (959 g, 7.34 mol) at 0° C. with a dry-ice acetone trap to recover the 1233zd vapor. The reaction progress is monitored by GC until the completion of starting material (1233zd); the excess chlorine was washed away with sodium sulfite solution then water once after completion. The crude 233da (1462 g, 98.8% yield) obtained was essentially pure (99.6% pure) and used was without any further purification in later examples.

EXAMPLE 2

Preparation of 233da

In a manner as described in Example 1, chlorine gas (650 g, 9.15mol) was bubbled into the trans-1233zd (1011 g, 7.75mol) at 0° C. The 233da was formed, yielding 1525 g, 97.8% yield, at 99.0% pure.

EXAMPLE 3

Preparation of 233da 15.5 g of $SbCl_5$ (mol) in 450 mL Monel autoclave was added 18.0 g of anhydrous HF under nitrogen atmosphere and heated to 90° C. for 2 hours. The pressure stopped increasing and cooled to 0° C. and vented under nitrogen atmosphere through a basic scrubber. Another 40.0 g of HF was charged into the autoclave at −78° C. followed by 30.0 g of 1,1,1,2,3,3-hexachloropropane.

The mixture was sealed and heated to 100° C. for 15 h. The mixture was cooled to 0° C. and vented through a basic scrubber solution. The mixture inside the autoclave was diluted with 40 mL of DI water and separated from the separator funnel. The organic layer was washed with DI water twice then diluted NaHCO$_3$ solution. 9.5 g of brown liquid was collected, which contained 38.6% 233da and a mixture of dichloro-trifluoro-propene isomers, cis-1223xd (52.2%) and trans-1223xd (9.2%), as determined by NMR analysis.

EXAMPLE 4

Preparation of cis-1233zd

The vessel for this reaction is essentially a distillation set-up, consisting of a four-necked 3000 mL flask fitted with an addition funnel, thermometer, mechanic stirrer and 2-foot reflux condenser controlled at 36° C. to 41° C. connected a distillation take-off adapter then to dry-ice acetone trap. Distillate and any material which passed by the condenser was collected in a cold trap at less than −50° C. The 233da used in herein was at least 99% pure.

The flask was charged with 2000 mL DI water, 20 mL of conc. HCl, and 428 g zinc dust. A total of 652 g, 3.23 mol of 233da was added over 4 to 5h, starting at 55° C. and increasing to 80° C. to 82° C. after addition is complete. The reaction temperature was at 80° C. to 82° C. for 30 to 45 min. The cold trap contained 362.0 g liquid (85.8% yield), which analyzed as 42.4% cis-1233zd, 51.8% trans-1233zd, 1.2% CF$_3$CCl=CHCl (HCFC-1223), and 4.3% 233da.

EXAMPLE 5

Preparation of cis-1233zd

In a manner as described in Example 4, 323 g zinc dust and 497 g of 96.1% pure 233da were reacted at a reaction temperature of from 55° C. to 65° C. for a total reaction time of 5 h. The cold trap contained 300 g of 1233zd isomers (93.2% yield) with 38.2% cis-1233zd, 60.4% trans-1233zd, 0.5% HCFC-1223, and 0.6% 233da.

EXAMPLE 6

Preparation of cis-1233zd

The reactor for this example is essentially a distillation set-up, consisting of a 100 mL flask fitted with an addition funnel, thermometer, and 6 inch packed column to which is attached a distillation take-off adapter having a condenser controlled at 12° C. to 13° C. Distillate and any material which passed by the condenser was collected in a cold trap at less than −50° C. The 233da was 93% pure and obtained by the chlorination of trans-1233zd process.

The flask was charged with 40 mL isopropanol, 5 drops of conc. HCl, and 11 g zinc dust. A total of 13.0 g of 233da was added over 40 minutes, starting at a reaction temperature of 75° C. and increasing to 82° C. After the 233da addition was complete, heating at 82° C. was continued for one hour. Finally, to make sure that all of the cis-isomer had been collected, the temperature of the pot was increased to 90° C. The cold trap contained 7.0 g liquid, which analyzed as 27.3% cis-1233zd and 72.7% trans-1233zd (70% total yield for 1233zd isomers).

EXAMPLE 7

Preparation of cis-1233zd

In a manner as described in Example 8, 40 mL DI water, 5 drops of conc. HCl, 11 g zinc dust and 11.7 g of 93% pure 233da were reacted at a temperature of from 75° C. to 80° C. for a total reaction time of 4 h. The cold trap contained 6.4 g of liquid (84% yield) with 48% cis-1233zd and 52% trans-1233zd.

EXAMPLE 8

Preparation of cis-1233zd

In a manner as described in Example 8, 40 mL pyridine, 5 drops of conc. HCl, 12.7 g zinc dust and 12.4 g of 93% pure 233da were reacted at a temperature range of from 35° C. to 80° C. for a total reaction time of 2 h. The cold trap contained 6.4 g of liquid with 38.5% cis-1233zd, 54.5% trans-1233zd, and 7% 233da.

EXAMPLE 9

Preparation of cis-1233zd

In a manner as described in Example 8, 40 mL isopropanol, 5 drops of conc. HCl, zinc copper alloy, made from 12.3 g CuCl and 8.1g zinc in THF (see, J. Org. Chem., 1970, 2057) and 10.0 g of 93% pure 233da were reacted at a temperature range of 75° C. to 80° C. for a total reaction time of 3 h. The cold trap contained 8.4 g of liquid with 14.8% cis-1233zd, 19.3% trans-1233zd, 28.9% isopropanol and 33.1% THF.

EXAMPLE 10

Preparation of cis-1233zd

In a manner as described in Example 8, 40 mL DMF, 0.1g CuI, 8.1 g zinc dust and 10.0 g of 93% pure 233da were reacted at a temperature range of 80° C. to 90° C. for a total reaction time of 3 h. The cold trap contained 4.7 g of 1233zd isomers (72% yield) with 41% cis-1233zd and 59% trans-1233zd.

EXAMPLE 11

Preparation of cis-1233zd

In a manner as described in Example 8, 40 mL DI water, 5 drops of conc. HCl, zinc-copper alloy (made from 8.1 g zinc dust and 0.5g CuCl in THF) and 10.0 g of 93% pure 233da were reacted at a temperature range of 75° C. to 80° C. for a total reaction time of 3 h. The cold trap contained 4.0 g of 1233zd isomers (62% yield) with 28% cis-1233zd and 72% trans-1233zd.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A process for the preparation of cis-1-chloro-3,3,3-trifluoropropene comprising the steps of (a) providing $CF_3CHClCHCl_2$ (HCFC 233da), and (b) treating the HCFC 233da with a dechlorinating agent to produce a mixture of compounds including up to 48% by weight of cis-1-chloro-3,3,3-trifluoropropene (cis-1233zd).

2. The process of claim 1, wherein the compound cis-1-chloro-3,3,3-trifluoropropene is isolated from the mixture of compounds produced in the process.

3. The process of claim 1, wherein the dechlorinating agent is selected from the group consisting of zinc, zinc compounds, a mixture of zinc compounds, copper, magnesium, and a zinc/copper alloy, and mixtures thereof.

4. The process of claim 3, wherein the dechlorinating agent comprises zinc dust.

5. The process of claim 3, wherein the dechlorinating agent comprises a zinc-copper alloy.

6. The process of claim 5, wherein the zinc-copper alloy dechlorinating agent comprises a mixture of zinc dust and cuprous iodide.

7. The process of claim 1, wherein a solvent is used in the process.

8. The process of claim 7, wherein the solvent is selected from the group consisting of alcohols, ethers, amides, carboxylic acids, water, and mixtures thereof.

9. The process of claim 8, wherein the solvent comprises water.

10. The process of claim 1, further comprising the use of a catalyst.

11. The process of claim 10, wherein the catalyst is selected from the group consisting of mineral acids and mixtures thereof.

12. The process of claim 11, wherein the mineral acid catalyst comprises HCl.

13. The process of claim 10, wherein the catalyst is selected from the group consisting of the Lewis acids and mixtures thereof.

14. The process of claim 13, wherein the Lewis acid catalyst comprises a metal salt or mixture of metal halide salts.

15. The process of claim 14, wherein the metal salt comprises a zinc halide salt.

16. The process of claim 15, wherein the zinc halide salt comprises zinc chloride.

17. The process of claim 14, wherein the metal salt comprises a tin halide salt.

18. The process of claim 17, wherein the tin halide salt comprises tin chloride.

19. The process of claim 7, wherein the reaction temperature range is less than the boiling point of the solvent.

20. A process for the preparation of cis-1-chloro-3,3,3-trifluoropropene (1233zd(Z)) comprising the steps of:
   (a) mixing a combination comprising zinc, solvent, and catalyst;
   (b) heating the mixture to within a few degrees of the predetermined reaction temperature;
   (c) adding 233da to the heated mixture in step (b) in a manner that controls the reaction temperature;
   (d) running the reaction and adding 233da as need; and
   (e) collecting the 1233zd(Z) as it is produced at a yield of up to about 48% by weight.

21. The process of claim 20, wherein the 233da is added mechanically at a set rate that is slow enough to maintain the reaction temperature.

22. The process of claim 20, wherein the reaction heating is continued for a time to ensure that all the 233da has reacted.

* * * * *